United States Patent
Pai et al.

(10) Patent No.: US 11,064,929 B2
(45) Date of Patent: Jul. 20, 2021

(54) FLEXIBLE ELECTRODE TIP WITH HALO IRRIGATION

(71) Applicant: St. Jude Medical, Cardiology Division, Inc., St. Paul, MN (US)

(72) Inventors: Sameer D. Pai, Plymouth, MN (US); Andrew R. Oliverius, Eagan, MN (US); Troy T. Tegg, Elk River, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 537 days.

(21) Appl. No.: 14/969,272

(22) Filed: Dec. 15, 2015

(65) Prior Publication Data

US 2016/0183821 A1 Jun. 30, 2016

Related U.S. Application Data

(60) Provisional application No. 62/098,561, filed on Dec. 31, 2014.

(51) Int. Cl.
| | | |
|---|---|---|
| A61B 18/12 | (2006.01) | |
| A61B 5/283 | (2021.01) | |
| A61B 18/14 | (2006.01) | |
| A61B 5/00 | (2006.01) | |
| A61B 5/287 | (2021.01) | |
| A61B 18/02 | (2006.01) | |
| A61B 18/24 | (2006.01) | |
| A61M 3/02 | (2006.01) | |
| A61B 18/00 | (2006.01) | |

(52) U.S. Cl.
CPC ............ *A61B 5/283* (2021.01); *A61B 5/287* (2021.01); *A61B 5/6852* (2013.01); *A61B 18/1492* (2013.01); *A61B 18/02* (2013.01); *A61B 18/24* (2013.01); *A61B 2018/00029* (2013.01); *A61B 2018/00351* (2013.01); *A61B 2018/00577* (2013.01); *A61B 2018/0212* (2013.01); *A61B 2218/002* (2013.01); *A61M 3/0279* (2013.01)

(58) Field of Classification Search
CPC ..... A61B 18/02; A61B 18/1492; A61B 18/24; A61B 2018/00029; A61B 2018/00351; A61B 2018/00577; A61B 2018/0212; A61B 2218/002; A61B 2562/0209; A61B 5/042; A61B 5/0422; A61B 5/6852
See application file for complete search history.

(56) References Cited

U.S. PATENT DOCUMENTS

| | | | |
|---|---|---|---|
| 6,371,955 B1* | 4/2002 | Fuimaono | A61B 18/1492 606/29 |
| 7,815,635 B2* | 10/2010 | Wittkampf | A61B 18/1492 606/41 |
| 8,187,267 B2 | 5/2012 | Pappone et al. | |
| 2003/0004506 A1* | 1/2003 | Messing | A61B 18/1492 606/41 |
| 2004/0019350 A1* | 1/2004 | O'Brien | A61B 18/14 606/41 |

(Continued)

*Primary Examiner* — Daniel W Fowler
(74) *Attorney, Agent, or Firm* — Dykema Gossett PLLC (57) ABSTRACT

The instant disclosure relates generally to a tip electrode for delivering irrigant to a distal portion of the tip electrode and irrigated catheter tips incorporating such a tip electrode. The distal portion of the tip electrode can have additional fluid ports on the distal edge of the tip to provide additional fluid flow to that region.

18 Claims, 8 Drawing Sheets

(56) References Cited

U.S. PATENT DOCUMENTS

| | | | |
|---|---|---|---|
| 2008/0275428 A1* | 11/2008 | Tegg | A61B 5/0084 604/533 |
| 2010/0152731 A1 | 6/2010 | de la Rama et al. | |
| 2010/0331658 A1* | 12/2010 | Kim | A61B 18/1492 600/373 |
| 2011/0009857 A1* | 1/2011 | Subramaniam | A61B 18/1492 606/33 |
| 2011/0282342 A1* | 11/2011 | Leo | A61B 18/1492 606/33 |

* cited by examiner

FIG. 14 ional application No. 62/098,561, filed Dec. 31, 2014, which is
FLEXIBLE ELECTRODE TIP WITH HALO IRRIGATION

CROSS-REFERENCE TO RELATED APPLICATIONS

This application claims the benefit of U.S. provishereby incorporated by reference as though fully set forth herein.

BACKGROUND a. Field

The instant disclosure relates generally to a tip electrode for delivering irrigant to a distal portion of the tip electrode and irrigated catheter tips incorporating such a tip electrode.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The proximal end of the catheter can be manipulated to guide the catheter through a patient's vasculature. The distal tip can be deflected by a pull wire attached at the distal end of the catheter that extends to a control handle that controls the application of tension on the pull wire.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include radio frequency (RF) ablation, cryoablation, laser ablation, chemical ablation, high-intensity focused ultrasound-based ablation, microwave ablation, etc. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents stray errant conduction signals that can form the basis for arrhythmias.

Because RF ablation can generate significant heat, which if not controlled can result in excessive tissue damages, such as steam pop, tissue charring, and the like, it can be desirable to monitor the temperature of ablation electrode assemblies. It can also be desirable to include a mechanism to irrigate the ablation electrode assemblies and/or targeted areas in a patient's body with biocompatible fluids, such as saline solution. The use of irrigated ablation electrode assemblies can also prevent the formation of soft thrombus and/or blood coagulation, as well as enable deeper and/or greater volume lesions as compared to conventional, non-irrigated catheters at identical power settings.

The foregoing discussion is intended only to illustrate the present field and should not be taken as a disavowal of claim scope.

BRIEF SUMMARY

In one embodiment, a catheter tip electrode can comprise a flexible electrode structure configured to flex upon application of an external force, a distal end portion adjacent the flexible electrode structure and defining a distal end, and at least one halo irrigation opening configured to allow irrigant to pass therethrough in a circumferential pattern about the flexible electrode structure and proximate the distal end.

In another embodiment, a flexible tip electrode can comprise a proximal stem, an electrode wall, and an electrode cap, wherein the electrode cap comprises at least one halo irrigation opening configured to allow irrigant to pass therethrough in a circumferential pattern about the flexible electrode structure and proximate the distal end.

In yet another embodiment, a catheter assembly can comprise a catheter body and a flexible tip electrode comprising a proximal stem, an electrode wall, and an electrode cap. The electrode cap can comprise a plurality of irrigation channels and a plurality of irrigation ports. The flexible tip electrode can be coupled to a distal end of the catheter body.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, medical instruments may be used in many orientations and positions, and these terms are not intended to be limiting and absolute.

Figure 1:
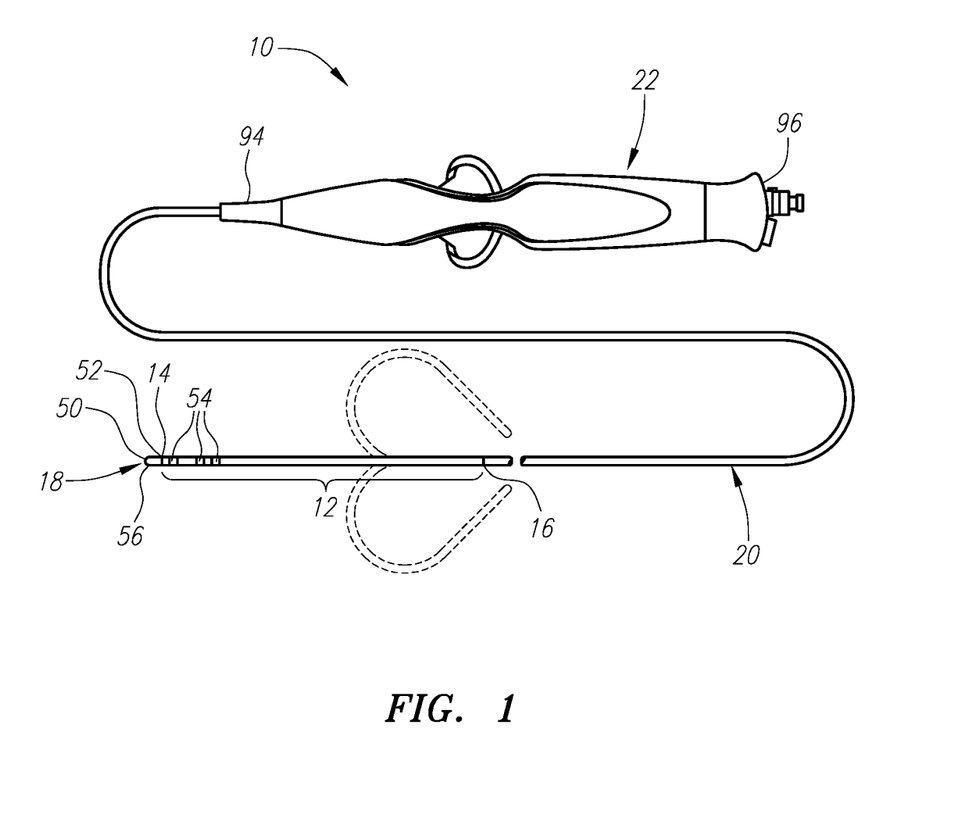
FIG. 1 is a schematic view of a catheter incorporating a deflectable catheter shaft section in accordance with an embodiment.

FIG. 1 generally illustrates a deflectable electrophysiology catheter 10 that comprises a deflectable catheter shaft section 12 in accordance with an embodiment. Deflectable catheter shaft section 12 comprises an elongated body having a distal end 14 and a proximal end 16. In its most general form, catheter 10 further comprises a tip assembly 18 located at the distal end 14 of the deflectable catheter shaft section 12, a proximal catheter shaft section 20 located at the proximal end 16 of the deflectable catheter shaft section 12, and a handle assembly 22. Catheter 10 may be used in any number of diagnostic and therapeutic applications, such as the recording of electrograms in the heart, the performance of a cardiac ablation procedure, and other similar applications/procedures. Accordingly, one of ordinary skill in the art will recognize and appreciate that the inventive deflectable catheter shaft section and method of manufacturing the same can be used in any number of diagnostic and therapeutic applications.

Still referring to FIG. 1, deflectable catheter shaft section 12 is disposed between the tip assembly 18 and the proximal catheter shaft section 20. The length and diameter of the deflectable catheter shaft section 12 can vary according to the application. Generally, the length of the deflectable catheter shaft section 12 can range from about 2 inches (50.8 mm) to about 6 inches (152.4 mm) and the diameter of the deflectable catheter shaft section 12 can range from about 5 French to about 12 French. The diameter of the deflectable catheter shaft section 12 can be about 7 French in accordance with some embodiments. Although these particular dimensions are mentioned in particular, the dimensions of the deflectable catheter shaft section 12 can vary in accordance with various applications of the deflectable catheter shaft section 12. The deflectable catheter shaft section 12 can be configured for deflection independent of the proximal catheter shaft section 20.

Tip assembly 18 comprises a tip electrode 56 having a distal end 50 and a proximal end 52. Tip electrode 56 may be configured for various functions and may include, without limitation, an active outer surface that is configured for exposure to blood and/or tissue. The tip electrode 56 may be affixed to distal end 14 of the deflectable catheter shaft section 12 in a number of ways. For instance, the tip electrode 56 may be bonded to an inner radial surface of the deflectable catheter shaft section 12 using an epoxy material. As used herein, the term "radial surface" means a surface at a radial distance from a central axis or a surface developing uniformly around a central axis (for example, but without limitation, an arcuate surface, an annular surface, or a cylindrical surface). The tip electrode 56 of the tip assembly 18 may have a recess (not shown) formed therein that is sufficiently sized and configured to receive a wire (not shown) that is connected to the tip electrode 56. One end of the wire is connected to the tip electrode 56 and the other end is connected to, for example, monitoring or recording or ablation devices, such as a radiofrequency (RF) generator. The wire is typically a pre-coated wire that is insulated from other components in the tip assembly 18. The tip electrode 56 of the tip assembly 18 may further include a recess (not shown) formed therein that is configured to receive a thermocouple (not shown). The thermocouple may be configured to measure the temperature of the tip electrode 56, targeted tissue, and/or the interface therebetween and provide feedback to the monitoring or recording or ablation devices described hereinabove. The tip electrode 56 may further include a fluid lumen configured as a passageway for irrigation fluid.

Proximal catheter shaft section 20 can also include one or more lumens (not shown). Generally, proximal catheter shaft section 20 can include a single lumen. Proximal catheter shaft section 20 can also be constructed of a series of polymer layer(s) and braid structure(s). In particular, one or more wires wound to form a cylindrical braid structure can substantially surround the one or more lumens of proximal catheter shaft section 20. In addition, a polymeric material, such as polyurethane, nylon, or various types of plastic materials such as polyether block amides offered under the trademark PEBAX®, or any other suitable material, can also substantially surround the one or more lumens of proximal catheter shaft section 20. Regardless of the material used, the material must have capability to be displaced or to shrink when subjected to a process, such as for example, a heating process that is performed. The mechanical properties of the proximal catheter shaft section 20 can also be varied by varying the properties of the cylindrical braid structure(s) and the polymeric material (e.g., dimension of the cylindrical braid structure and/or durometers of the polymers). Additionally, the mechanical properties of the proximal catheter shaft section 20 can be varied along the length of the proximal catheter shaft section 20 in accordance with some embodiments of the disclosure or can be substantially constant along the entire length of the proximal catheter shaft section 20 in accordance with other embodiments of the disclosure.

The handle assembly 22 is coupled to the proximal catheter shaft section 20 at its proximal end (disposed within handle assembly 22 and not shown). The handle assembly 22 is operative to, among other things, effect movement (i.e., deflection) of the deflectable catheter shaft section 12. The handle assembly 22 includes a distal end 94 and a proximal end 96.

The catheter 10 may include any number of other elements such as, for example and without limitation, thermocouples, thermistor temperature sensors, etc. for monitoring the temperature of targeted tissue and controlling the temperature.

Figure 2:
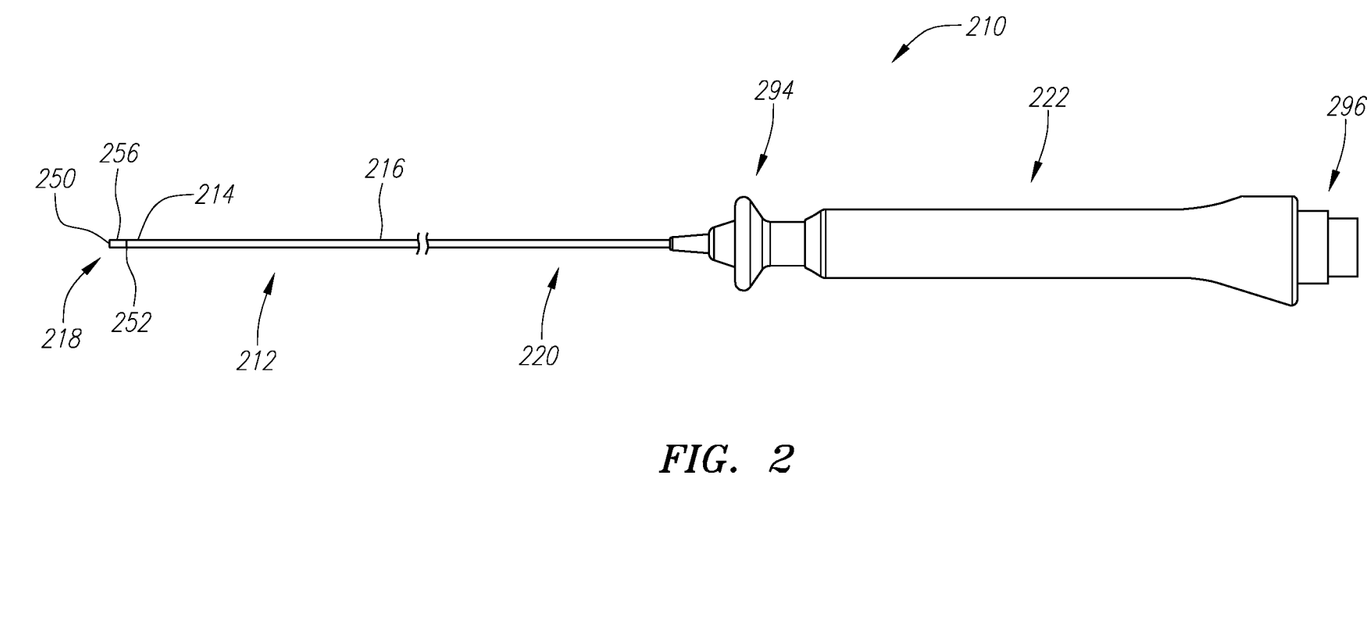
FIG. 2 is a schematic view of a catheter incorporating a deflectable catheter shaft section in accordance with another embodiment.

FIG. 2 generally illustrates another embodiment of a deflectable electrophysiological catheter 210. The embodiment of the catheter depicted in FIG. 2 comprises a handle assembly where a push/pull action is performed to deflect the deflectable catheter shaft section 212. The deflectable catheter shaft section 212 comprises an elongated body having a distal end 214 and a proximal end 216. The deflectable electrophysiological catheter 210 further comprises a tip assembly 218 located at the distal end of the deflectable catheter shaft section 214, a proximal catheter shaft section 220, and a handle assembly 222.

Deflectable catheter shaft section 212 is disposed between the tip assembly 218 and the proximal catheter shaft section 220. The length and diameter of the deflectable catheter shaft section 212 can vary according to the application. Generally, the length of the deflectable catheter shaft section 212 can range from about 2 inches (50.8 mm) to about 6 inches (152.4 mm) and the diameter of the deflectable catheter shaft section 212 can range from about 5 French to about 12 French. The diameter of the deflectable catheter shaft section 212 can be about 7 French in accordance with some embodiments. Although these particular dimensions are mentioned in particular, the dimensions of the deflectable catheter shaft section 212 can vary in accordance with various applications of the deflectable catheter shaft section 212. The deflectable catheter shaft section 212 can be configured for deflection independent of the proximal catheter shaft section 220.

Tip assembly 218 comprises a tip electrode 256 having a distal end 250 and a proximal end 252. Tip electrode 256 may be configured for various functions and may include, without limitation, an active outer surface that is configured for exposure to blood and/or tissue. The tip electrode 256 may be affixed to distal end 214 of the deflectable catheter shaft section 212 in a number of ways. For instance, the tip electrode 256 may be bonded to an inner radial surface of the deflectable catheter shaft section 212 using an epoxy material. As used herein, the term "radial surface" means a surface at a radial distance from a central axis or a surface developing uniformly around a central axis (for example, but without limitation, an arcuate surface, an annular surface, or a cylindrical surface). The tip electrode 256 of the tip assembly 218 may have a recess (not shown) formed therein that is sufficiently sized and configured to receive a wire (not shown) that is connected to the tip electrode 256. One end of the wire is connected to the tip electrode 256 and the other end is connected to, for example, monitoring or recording or ablation devices, such as a radiofrequency (RF) generator. The wire is typically a pre-coated wire that is insulated from other components in the tip assembly 218. The tip electrode 56 of the tip assembly 218 may further include a recess (not shown) formed therein that is configured to receive a thermocouple (not shown). The thermocouple may be configured to measure the temperature of the tip electrode 256, targeted tissue, and/or the interface therebetween and provide feedback to the monitoring or recording or ablation devices described hereinabove. The tip electrode 56 may further include a fluid lumen configured as a passageway for irrigation fluid.

Figures 3, 5:
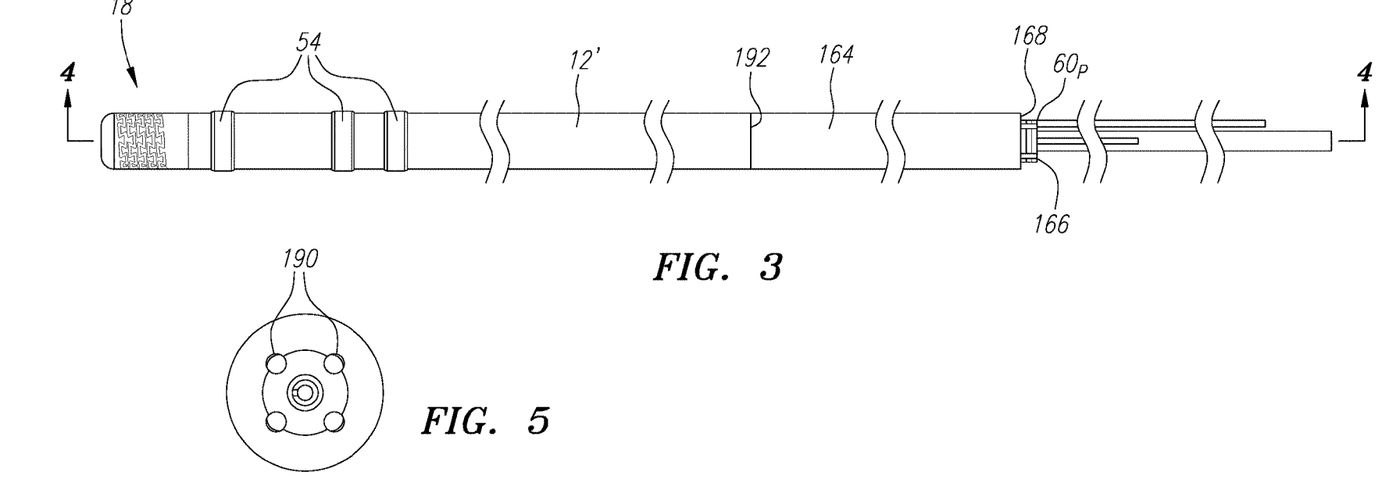
FIG. 3 is a fragmentary view of a deflectable catheter shaft section and an intermediate catheter shaft section.
FIG. 5 is an end view taken in the direction of line 5-5 of FIG. 4.
Figure 4:
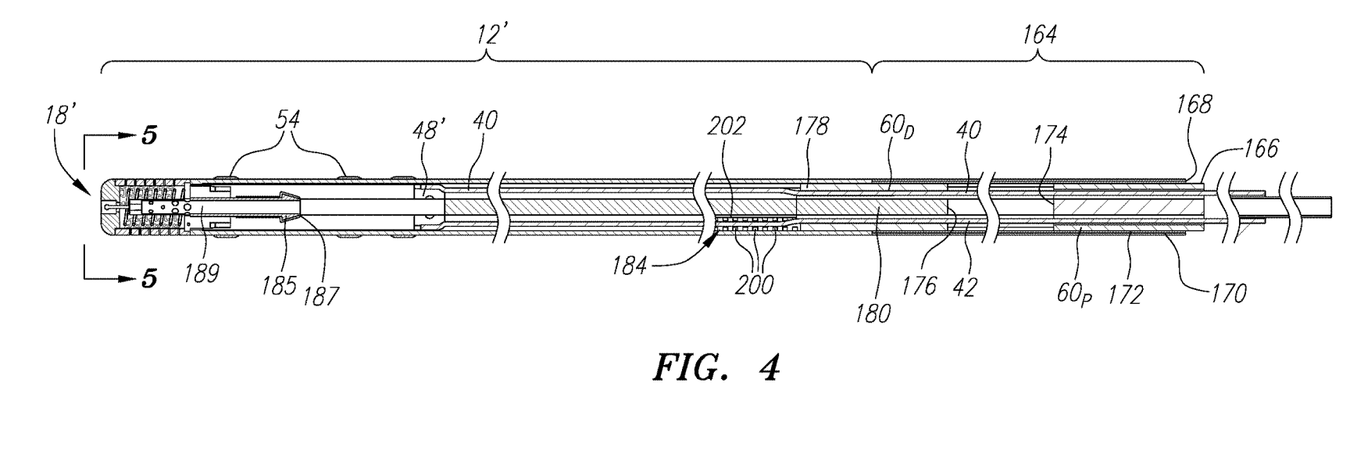
FIG. 4 is a cross-sectional view taken along line 4-4 of FIG. 3.

FIGS. 3 and 4 depict a deflectable catheter shaft section 12' similar to the deflectable catheter shaft section 12 shown to good advantage in, for example, FIGS. 1, and 2. As shown in FIGS. 3 and 4, the catheter shaft may include the deflectable catheter shaft section 12', an intermediate catheter shaft section 164, and a proximal catheter shaft section (not shown in FIGS. 3 and 4, but the proximal catheter shaft section, if present, would abut the right longitudinal end, as oriented in FIGS. 3 and 4, of the intermediate catheter shaft section 164). In this embodiment, two shaft couplers are used, including a proximal shaft coupler $60_P$ for coupling the proximal catheter shaft section to the intermediate catheter shaft section 164, and a distal shaft coupler $60_D$ for coupling the intermediate catheter shaft section 164 to the deflectable catheter shaft section 12'.

In at least one embodiment, the proximal catheter shaft section may comprise a portion of the handle assembly, e.g., the proximal catheter shaft section may comprise a pocket (not shown) sized and configured to receive a proximal shaft coupler $60_P$ and formed in the distal end 94 of handle assembly 22 seen in FIG. 1. In an alternative embodiment, it is possible, depending upon which handle assembly 22 is selected, that the handle assembly may connect to the proximal end 168 of the intermediate catheter section 164, or to the proximal end 166 of the proximal shaft coupler $60_P$. In these latter configurations, the intermediate catheter shaft section 164 would be analogous to the proximal catheter section shown in, for example, FIG. 1.

Referring more particularly to FIG. 4, additional details will be described. FIG. 4 is a cross-sectional view taken along line 6-6 of FIG. 3. Starting from the right side of FIG. 4 and moving leftward, a proximal end 166 of the proximal shaft coupler $60_P$ may be seen extending proximally beyond the proximal end 168 of the intermediate catheter shaft section. It is also possible to see that the intermediate catheter shaft section 164 may include a first shaft material 170 (e.g., PEBAX) and a second shaft material 172 (e.g., PEBAX or braided mesh). A first pull wire 40 may be seen extending along the upper portion of the proximal shaft coupler 60$_P$, and a second pull 42 wire may be seen extending adjacent a lower portion of the proximal shaft coupler 60$_P$. The portion of these pull wires 40, 42 extending from the proximal end 166 of the proximal shaft coupler 60$_P$ back to the handle assembly 22 (see, for example, FIG. 1) may have compression coils surrounding them. Additionally, there may be compression coils (not shown) extending between a distal end 174 of the proximal shaft coupler 60$_P$ and a proximal end 176 of the distal shaft coupler 60$_D$. These compression coils would be under compression (e.g., they may be compressed 0.070 in.) to help mitigate against undesirable deformation of the intermediate catheter shaft section 164 extending between the proximal and distal shaft couplers. In the embodiment shown, the compression coils do not extend through the proximal shaft coupler, but they could in an alternative embodiment.

Moving further leftward in FIG. 4, the distal shaft coupler 60$_D$, which is depicted as joining the intermediate catheter shaft section 164 (which, as discussed above, may extend to the handle assembly 22) to the deflectable catheter shaft section 12' that extends from the distal shaft coupler to the tip assembly 18'. As shown in FIG. 4, when the first pull wire 40 exits the distal end 178 of the distal shaft coupler 60$_D$, it enters a liner 182 (e.g., a thin-walled PTFE tube). The second pull wire 42, upon exiting the distal end 178 of the distal shaft coupler 60$_D$, extends through a bendable stiffening member (e.g., a 'coil pack' or a 'spring pack' or an 'uncompacted spring pack' or a 'deflection facilitator') 184, the proximal end of which is visible in FIG. 4.

Distal to the pull ring 48' in the configuration depicted in FIGS. 3 and 4 are a plurality of ring electrodes 54 followed distally by a tip assembly 18', including, for example, a flexible tip electrode from a Therapy™ Cool Flex™ ablation catheter manufactured by St. Jude Medical, Inc. of St. Paul, Minn. Additional details regarding a flexible electrode tip may be found in, for example, U.S. Pat. No. 8,187,267 B2 and United States patent application publication no. US 2010/0152731 A1, each of which is hereby incorporated by reference as though fully set forth herein. The tip assembly 18', as depicted in FIG. 4, also includes a barbed connector 185 that locks into a complementary pocket 187, thereby facilitating delivery of irrigant to a ported fluid distribution tube 189. FIG. 5 is an end view of the tip assembly 18' (looking in the direction of the arrows on line 7-7 of FIG. 4) and illustrates a plurality of irrigation ports 190 through the distal surface of the tip.

Figure 6:
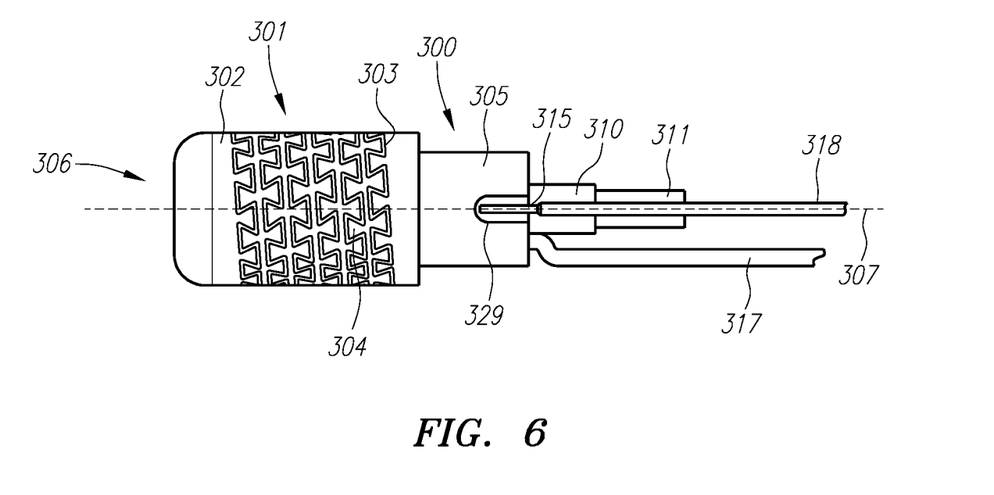
FIG. 6 is a fragmentary view of a flexible tip assembly in accordance with an embodiment.

In various embodiments, a catheter may comprise a flexible tip assembly, which may be positioned and/or constructed similar to tip assemblies 18 and/or 18' described above. One embodiment of a flexible tip assembly 300 is illustrated in FIG. 6. The flexible tip assembly 300 has a longitudinal axis 307 and can comprise a flexible tip electrode 301, an electrode wire 315, a stop tube 310, a fluid lumen manifold 311, and a thermal sensor 317. The flexible tip electrode 301 can comprise a tip electrode distal end 306, a proximal stem 305, a recess 329, and an electrode wall 302. The electrode wall 302 can comprise at least one linear gap 303. The at least one linear gap 303 can extend along an outer radial surface of the flexible tip electrode 301 and can form a variety of patterns on the outer radial surface of the flexible tip electrode 301. In one embodiment, the pattern is an interlocking dovetail pattern. The interlocking dovetail pattern can comprise a plurality of blocks 304 wherein each of the blocks comprises a head 332 and a neck 331 (see FIG. 7). Alternatively, the pattern can be and, in one embodiment, is any type of interlocking arrangement that provides for relative movement in the proximal and distal direction with regard to either all or part of tip assembly 108. For example, alternative patterns of the interlocking arrangement can be and, in one embodiment, is bulbous, trapezoidal, triangular, rectangular, and any other shape that creates an interlocking fit. Such features allow for the electrode 301 to flex when external force is applied thereto. When the terms such as "flexible" or "flex" are used with respect to a flexible tip assembly or flexible tip electrode, etcetera, it is to be understood that such an assembly or electrode is more flexible than a typical solid tip assembly or electrode which would be considered by those of ordinary skill in the art as rigid.

The electrode wire 315 is coupled to the recess 329 of the flexible tip electrode 301. The electrode wire 315 can be coupled to the flexible tip electrode 301 by soldering, adhesive, or other methods known in the art. The electrode wire 315 can be surrounded along part of its length by a wire coating 318. The wire coating 318 can electrically insulate the electrode wire 315 from other components of the catheter. The electrode wire 315 can be connected to, for example, monitoring or recording or ablation devices, such as a radiofrequency (RF) generator. The distal end of thermal sensor 317 can be positioned proximate the tip electrode distal end 306 and can be used to monitor the operating temperature of the flexible tip electrode 301 or the temperature of tissue adjacent the flexible tip electrode 301. The stop tube 310 may be coupled to the fluid lumen manifold 311 and configured to interact with a portion of the flexible tip electrode 301 to control the distance that a distal end of the fluid lumen manifold 311 can extend into the flexible tip electrode 301.

Figure 7:
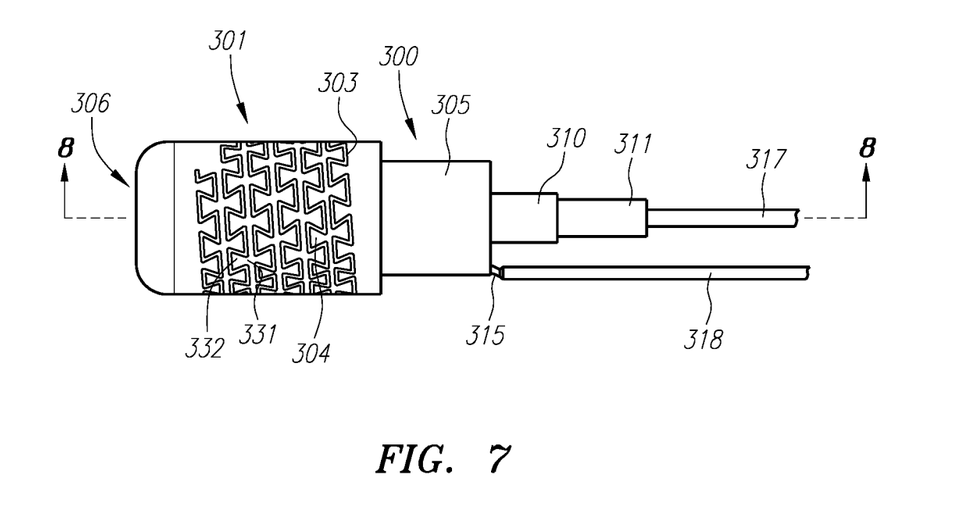
FIG. 7 is a fragmentary view of the flexible tip assembly depicted in FIG. 6 rotated 90 degrees about a longitudinal axis of the flexible tip assembly.

FIG. 7 illustrates the embodiment of the flexible tip assembly 300 shown in FIG. 6 rotated 90 degrees about a longitudinal axis of the flexible tip assembly 300. The electrode wire 315 and the wire coating 318 covering a portion of the electrode wire is illustrated traveling parallel to a longitudinal axis of the flexible tip assembly 300. The wiring of thermal sensor 317 is illustrated traveling parallel to the longitudinal axis of the flexible tip assembly 300 and in the illustrated configuration is offset from the electrical wire 315 by 90 degrees around the outer radial surface of the flexible tip electrode 301.

Figure 8:
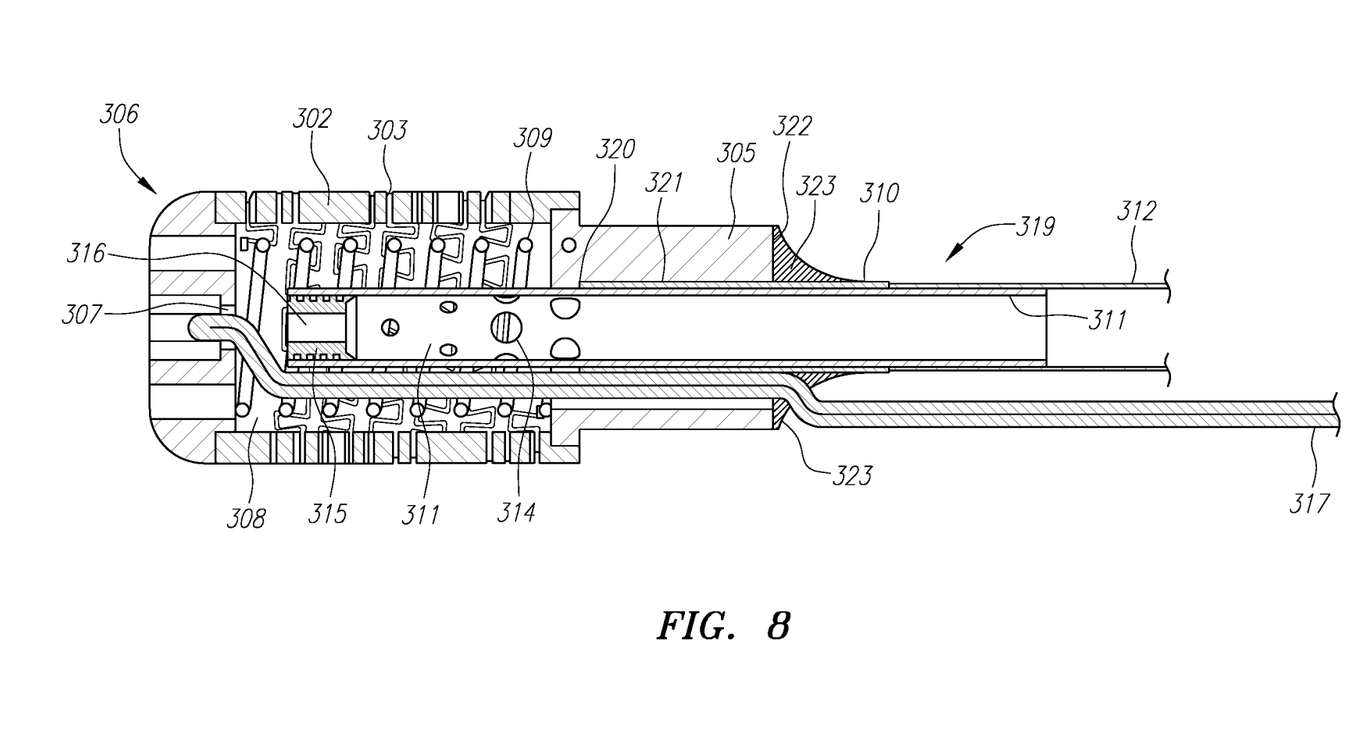
FIG. 8 is a cross-sectional view of the flexible tip assembly of FIGS. 6 and 7 taken along line 8-8.

FIG. 8 shows a cross-sectional view of the embodiment illustrated in FIG. 7 taken along line 19-19. The flexible tip assembly 300 comprises the flexible tip electrode 301, a manifold assembly 319, and the thermal sensor 317. The flexible tip electrode comprises a center cavity 308, a coil 309, an electrode wall 302, a linear gap 303, a proximal stem 305, a ledge feature 320, and a proximal face 322. The coil 309 is configured to be located within the center cavity 308 of the flexible tip electrode 301 and can be configured to provide structural integrity to the flexible tip electrode and to bias the flexible tip electrode 301 into pre-determined arrangements. The coil 309 can bias the flexible tip electrode 301 in a longitudinal direction or in a pre-bent configuration. In one embodiment, the coil 309 can comprise a resilient material such as stainless steel and/or a shape memory material such as nitinol. The electrode wall 302 can comprise at least one linear gap 303. In the illustrated embodiment the at least one linear gap extends from an outer radial surface of the electrode wall 302 through an inner radial surface of the electrode wall 302. When the at least one linear gap 303 extends through the electrode wall 302 as illustrated, irrigant delivered to the flexible tip electrode 301 can pass through the electrode wall 302. The irrigant is fluidly coupled to the area surrounding the outer radial surface of the flexible tip electrode 301. The proximal stem 305 of the flexible tip electrode 301 may couple the tip assembly 300 to the deflectable catheter shaft section 12 (see FIG. 1) by way of adhesive, epoxy, reflowed shaft polymer material, and/or other bonding materials or techniques. Further, the proximal stem 305 can comprise an inner surface 321, a ledge feature 320 and a proximal face 322. The inner surface 321 of the proximal stem 305 can define a lumen through which the manifold assembly can pass. The ledge feature 320 may be an annular or partially annular lip or protrusion from inner surface 321 that is sized and configured to interact with a manifold assembly, such as manifold assembly 319 illustrated here, such that the manifold assembly 319 can be inserted a predetermined distance into the center cavity 308. As noted above, the ledge feature 320 can comprise a ridge or narrowing of the inner surface 321 of the proximal stem 305. In other embodiments the ledge feature can comprise a non-continuous feature to restrict the movement of the stop tube 310 past a certain point in the proximal stem 305 of the flexible tip electrode 301. The proximal face 322 of the proximal stem 305 can be configured to be used as a bonding surface for a proximal adhesive 323. The proximal adhesive 323 can be used to couple the manifold assembly 319 to the proximal stem 305 of the flexible tip electrode 301.

Referring still to FIG. 8, the manifold assembly 319 can comprise the fluid lumen manifold 311 and the stop tube 310. The fluid lumen manifold 311 can comprise a plurality of sideholes 314 in a distal section. The plurality of sideholes 314 can be configured to deliver irrigant into the center cavity 308 in a desired manner. As a result, in some embodiments, more proximally located sideholes 314 can be larger in diameter than the sideholes 314 found more distally on the fluid lumen manifold 311. In other embodiments the more proximally located sideholes 314 can be smaller in diameter than the sideholes 314 found more distally on the fluid lumen manifold 311. In yet other embodiments the plurality of sideholes 314 can comprise the same general diameter. The stop tube 310 can be configured to couple to the fluid lumen manifold 311 through the use of adhesive or other process. The stop tube 310 can be further configured to interact with the ledge feature 320 of the proximal stem 305 to control the length the distal portion of the manifold assembly 319 is inserted into the center cavity 308 of the flexible tip electrode 301. A proximal end of the stop tube 310 can extend past the proximal face 322 of the proximal stem 305 when the stop tube 310 is butted to the ledge feature 320. The stop tube 310 can provide a ledge adjacent the proximal face 322 so that when the proximal adhesive 323 is applied to the proximal face 322 of the proximal stem 305 the stop tube 310 will keep the adhesive from an outer surface of the fluid lumen manifold 311. The stop tube 310 can be configured to provide an appropriate length so that when an adhesive is applied in a semi-liquid state, the adhesive's profile is entirely on a stop tube outer surface 348 and does not cover a proximal face of the stop tube 310 or an outer surface of a fluid lumen manifold. By keeping the adhesive away from the proximal face of the stop tube 310 the distance between the proximal face of the stop tube and other components of the flexible tip assembly can be kept to a known, consistent value. The manifold assembly 319 is further configured to couple to a fluid lumen, such as tapered fluid lumen 312. In at least one embodiment the tapered fluid lumen 312 can cover a proximal portion of the fluid lumen manifold 311 and abut the stop tube 310. While the manifold assembly 319 is depicted in the illustrated embodiment coupling to a flexible tip electrode 301, the manifold assembly disclosed herein can be used with any irrigated catheter tip. The manifold assembly 319 can be used to place a distal end of the manifold assembly 319 at a predetermined location within the tip electrode and/or to place a proximal end of the manifold assembly 319 a predetermined distance from a proximal end of the tip electrode.

In various embodiments, a catheter such as that described above may comprise a tip electrode including a flexible electrode structure and at least one halo irrigation opening defined in a distal end portion of the tip electrode. The one or more halo irrigation openings may be configured to provide a ring-like or other circumferentially defined pattern of irrigant near a distal end of the tip assembly. The one or more halo irrigation openings can provide additional fluid flow to regions of the electrode tip. The additional irrigation openings on the distal edge of the tip can increase fluid flow in areas where irrigation fluid flow was less than optimal.

Figure 9:
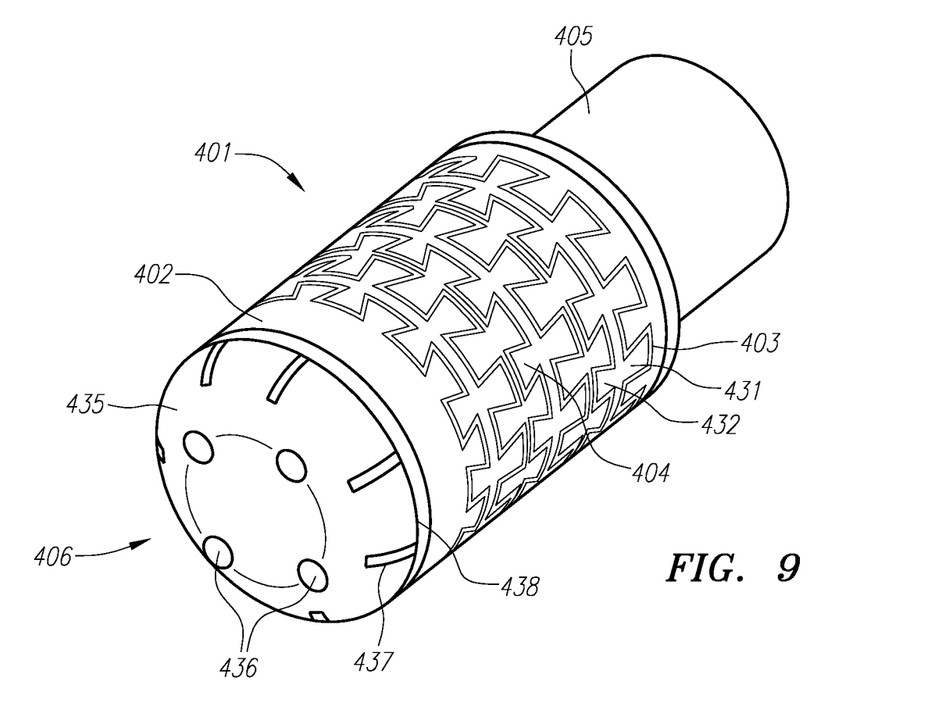
FIGS. 9-12 are isometric views of various embodiments of a flexible tip electrode.

Various non-limiting examples of such tip electrodes may include the following. FIG. 9 illustrates an embodiment of a flexible tip electrode 401. The flexible tip electrode 401 comprises a proximal stem 405, a flexible electrode structure, such as electrode wall 402, and a distal end portion, such as electrode cap 435. The proximal stem 405 can be configured to couple the flexible electrode tip 401 to a catheter body or other medical device. The electrode wall 402 can comprise at least one linear gap 403. The at least one linear gap 403 can extend along an outer radial surface of the flexible tip electrode 401 and can form a variety of patterns on the outer radial surface of the flexible tip electrode 401. In one embodiment, the pattern is an interlocking dovetail pattern. The interlocking dovetail pattern can comprise a plurality of blocks 404 wherein each of the blocks 404 comprises a head 432 and a neck 431.

Alternatively, the pattern can be and, in one embodiment, is any type of interlocking arrangement that provides for relative movement in the proximal and distal direction with regard to the flexible tip electrode 401. For example, alternative patterns of the interlocking arrangement can be and, in one embodiment, is bulbous, trapezoidal, triangular, rectangular, and any other shape that creates an interlocking fit. Such features allow for the electrode 401 to flex when external force is applied thereto.

The electrode cap 435 comprises a plurality of irrigation ports 436, a cap ridge 438, and at least one halo irrigation opening, such as irrigation slots 437. In the illustrated embodiment, the plurality of irrigation ports 436 can comprise four irrigation ports that are evenly distributed around a longitudinal axis of the flexible tip electrode 401. In other embodiments, the plurality of irrigation ports 436 can comprise only two irrigation ports that can be symmetrically located on the electrode cap 435 around the longitudinal axis. Other embodiments are also contemplated with varying numbers of irrigation ports and arrangement of irrigation ports around the electrode cap 435. The cap ridge 438 runs along a proximal portion of the electrode cap 435 and is sized and configured for positioning and coupling the electrode cap 435 to the electrode wall 402. The cap ridge 438 is further discussed and more completely shown in FIG. 14.

The irrigation slots 437 can comprise distally extending slots within the electrode cap 435 that is fluidly coupled with the center cavity of the flexible tip electrode 401. The irrigation slots 437 can be sized and configured to allow irrigant to flow from the center cavity of the flexible tip electrode 401 to an area external of the flexible tip electrode 401. In some embodiments, a proximal edge of the exterior opening of the irrigation slots 437 can be defined by a distal edge of the electrode wall 402. In other embodiments the proximal edge of the exterior opening of the irrigation slots 437 can be defined by the electrode cap 435 and be fluidly coupled to the inner cavity of the flexible tip electrode 401 through an inner passage within the electrode cap 435. In the illustrated embodiment, the irrigation slot 437s can comprise eight irrigation slots that are distributed around an outer circumference of the electrode cap 435. In the illustrated embodiment, pairs of the irrigation slots are situated on a proximal end of the electrode cap 405, between the plurality of irrigation ports 436. In other embodiments the irrigation slots can be equally spaced along the outer circumference of the electrode cap 435 or placed in other arrangements. The irrigation slots 437 can be configured to increase the amount of irrigant flowing through the electrode cap 435 and towards the distal end 406 of the flexible tip electrode 401. Moreover, irrigation slots 437 may be configured to deliver irrigant proximate the distal end 406 and at least partially towards a side of the electrode assembly such that irrigant is provided external the electrode 401 between the distal end 406 and the electrode wall 402.

Figure 10:
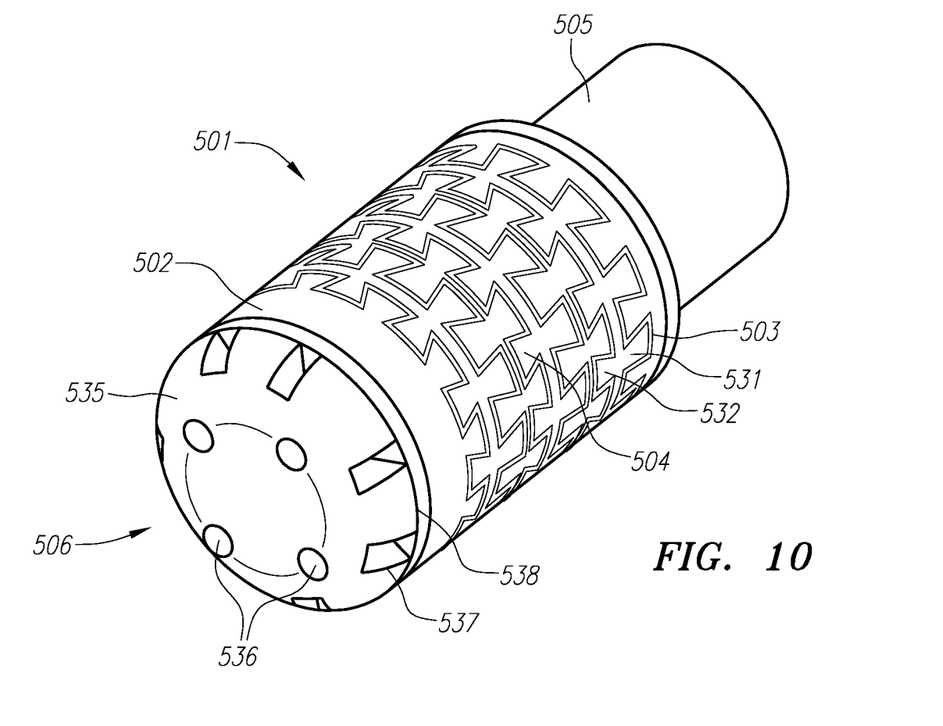

FIG. 10 illustrates another embodiment of a flexible tip electrode 501. The flexible tip electrode 501 comprises a proximal stem 505, a flexible electrode structure, such as electrode wall 402, and a distal end portion, such as electrode cap 535. The electrode wall 502 can comprise at least one linear gap 503 that can form an interlocking dovetail pattern. The interlocking dovetail pattern can comprise a plurality of blocks 504 wherein each of the blocks comprises a head 532 and a neck 531. The electrode cap 535 comprises a plurality of irrigation ports 536, a cap ridge 538, and at least one halo irrigation opening, such as irrigation slots 537. The irrigation slots 537 can comprise openings that can be fluidly coupled to an interior of the flexible tip electrode 501. The irrigation slots 537 can extend longitudinally from a proximal end of the electrode cap 535 to a more distal location along the electrode cap 535. In the illustrated embodiment, the width of the irrigation slots 537 can be around the same as the diameter of the plurality of irrigation ports 536. In other embodiments, the width of the at least one irrigation ports 536 can be either narrower or broader. The distally extending length of the irrigation slots 537 can also vary in other embodiments. In the illustrated embodiment, pairs of the irrigation slots are situated between the plurality of irrigation ports. In other embodiments the irrigation slots can be equally spaced along the outer circumference of the electrode cap 535 or placed in other arrangements. The irrigation slots 537 can be configured to increase the amount of irrigant that flowing through the electrode cap 535 and towards the distal end 506 of the flexible tip electrode 501.

Figure 11:
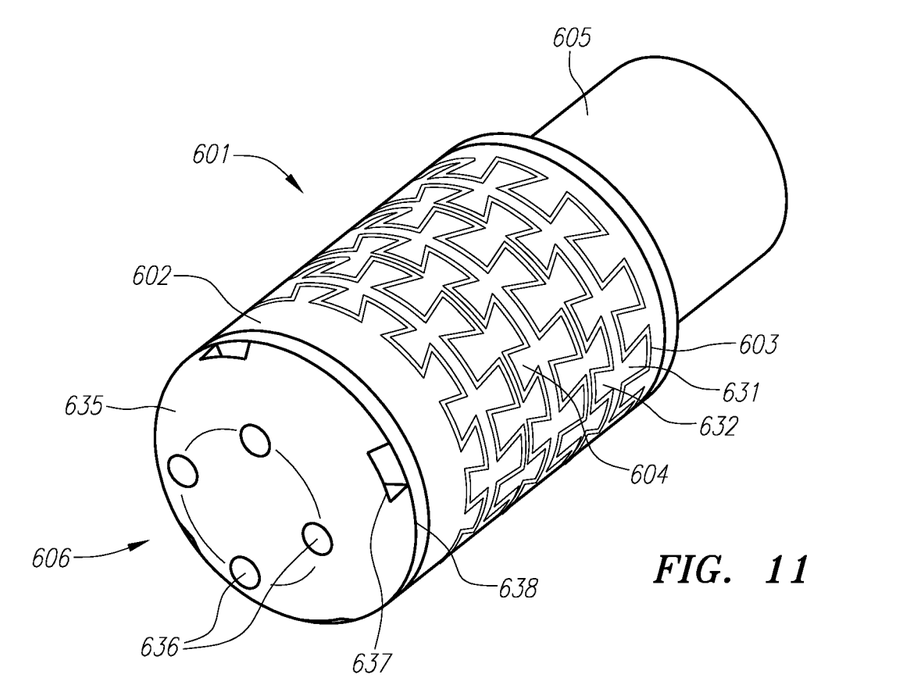

FIG. 11 illustrates yet another embodiment of a flexible tip electrode 601. The flexible tip electrode 601 comprises a proximal stem 605, a flexible electrode structure, such as electrode wall 402, and a distal end portion, such as electrode cap 635. The electrode wall 602 can comprise at least one linear gap 603 that can form an interlocking dovetail pattern. The interlocking dovetail pattern can comprise a plurality of blocks 604 wherein each of the blocks 604 comprises a head 632 and a neck 631. The electrode cap 635 comprises a plurality of irrigation ports 636, a cap ridge 638, and at least one halo irrigation opening, such as irrigation channels 637. The irrigation channels 637 can comprise openings that can be fluidly coupled to an interior of the flexible tip electrode 601. The irrigation channels 637 can extend longitudinally from a proximal end of the electrode cap 635 to a more distal location along the electrode cap 635. In the illustrated embodiment, the irrigation channels 637 can comprise opening that is wider than it extends longitudinally. In other embodiments, the width of the irrigation channels 637 can be either narrower or broader. The distally extending length of the irrigation channels 637 can also vary in other embodiments. In the illustrated embodiment, the electrode cap 635 comprises four irrigation channels. The four irrigation channels are equally spaced around an exterior circumference of the electrode cap. In other embodiments, the irrigation channels can vary in number and in spacing.

Figure 12:
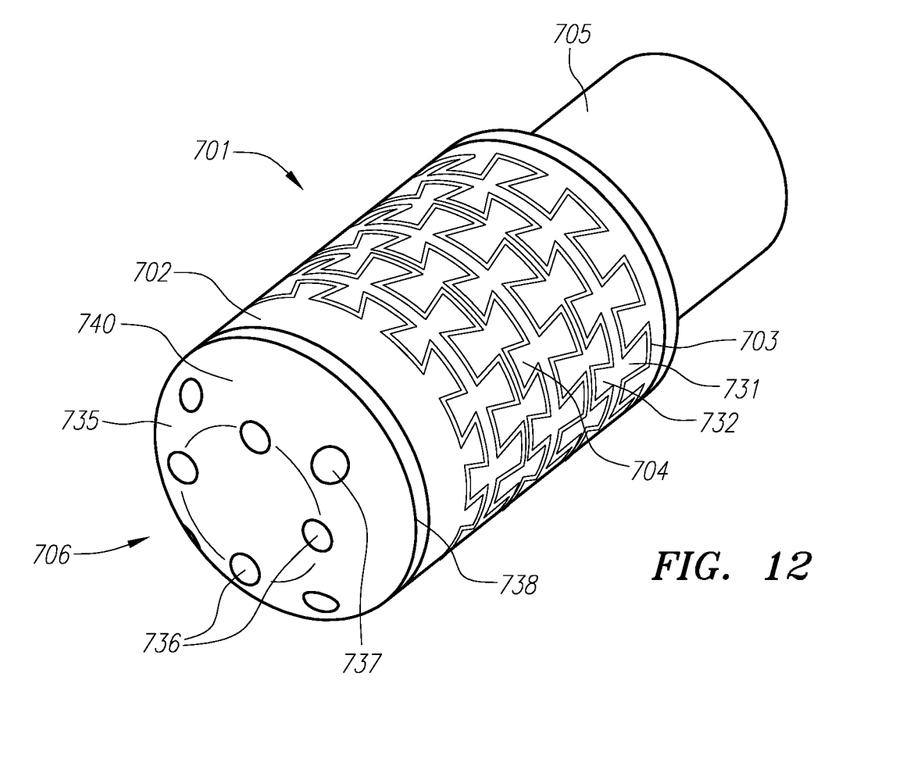

FIG. 12 illustrates another embodiment of a flexible tip electrode 701. The flexible tip electrode 701 comprises a proximal stem 705, a flexible electrode structure, such as electrode wall 402, and a distal end portion, such as electrode cap 735. The electrode wall 702 can comprise at least one linear gap 703 that can form an interlocking dovetail pattern. The interlocking dovetail pattern can comprise a plurality of blocks 704 wherein each of the blocks comprises a head 732 and a neck 731. The electrode cap 735 comprises a plurality of irrigation ports 736, a cap ridge 738, a cap transition 740, and at least one halo irrigation opening, such as irrigation holes 737. The irrigation holes 737 can comprise openings that can be fluidly coupled to an interior of the flexible tip electrode 701. Each of the irrigation holes 737 can comprise a circular or oval shaped opening on the distal end of the flexible tip electrode 701 and can comprise passageways through the electrode cap 735 to the electrode cavity. In one embodiment, the irrigation holes 737 can be positioned on the cap transition 740. The cap transition 740 can transition the electrode cap 735 from a distal most portion to the dimensions of the cap ridge 738. The cap transition can comprise a rounder portion, a sloped portion, a bevel, or other type of geometry that allows the distal facing portion of the electrode cap 735 to join with the cap ridge 738. By locating the irrigation holes 737 farther from a central axis of the flexible tip electrode 701 the irrigation holes 737 can be configured to provide additional irrigant to the area surrounding the distal end of the flexible tip electrode 701. In some embodiments the irrigation holes 737 can be angled such that fluid flowing through the flexible tip electrode 701 and the irrigation holes 737 exits the irrigation hole at an angle relative to the longitudinal axis of the flexible tip electrode 701. In the illustrated embodiment, the irrigation holes 737 can comprise four irrigation holes that can be evenly distributed around the cap transition 740 and the four irrigation holes can also be located an equal distance from the longitudinal axis of the flexible tip electrode 701. In other embodiments the electrode cap 735 can comprise different numbers of irrigation holes, the irrigation holes can be located in different areas of the electrode cap 735, and the spacing of the irrigation holes can vary depending on the desired effect from fluid moving through the irrigation holes.

Figure 13:
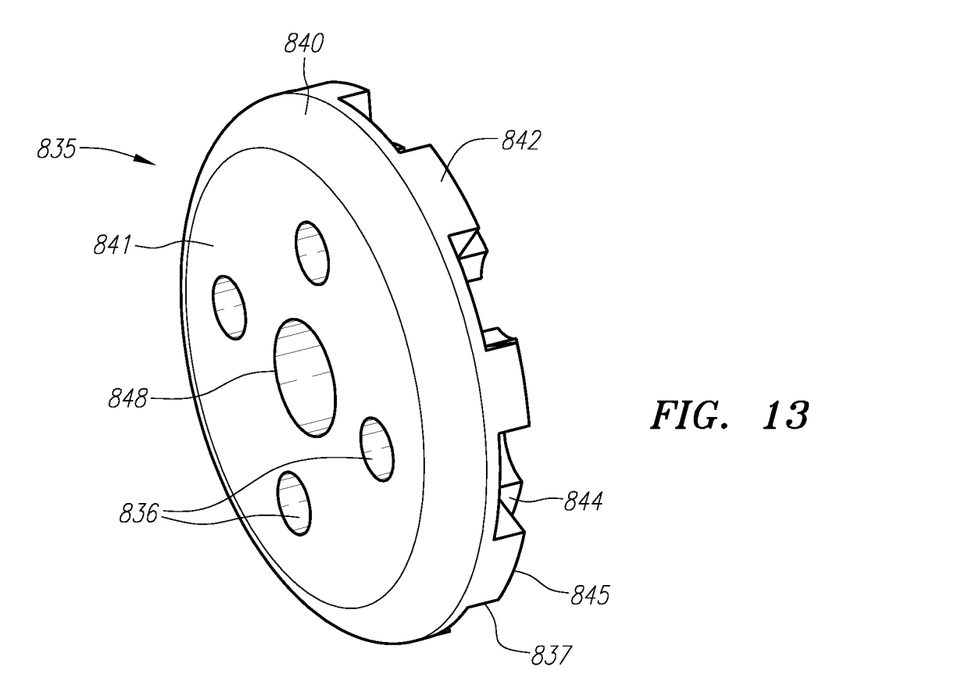
FIG. 13 is an isometric top view of an electrode cap.
Figure 14:
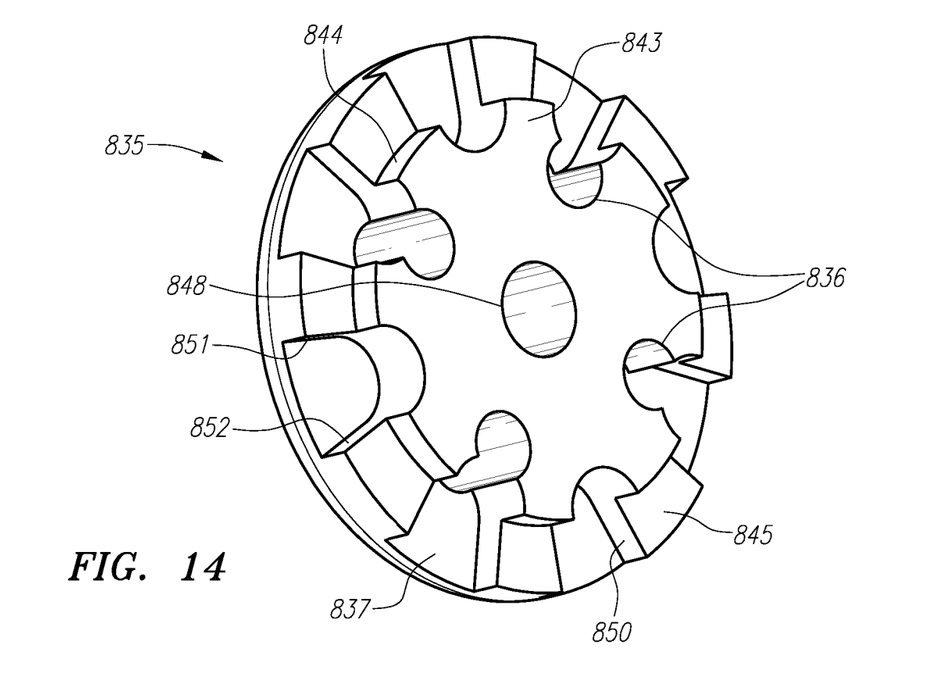
FIG. 14 is an isometric bottom view of the electrode cap illustrated in FIG. 13.

FIGS. 13 and 14 are a top and bottom isometric view of an electrode cap 835 according to at least one embodiment. The electrode cap 835 comprises a cap top 841, a cap transition 840, an outer cap edge 842 a cap bottom 843, a cap ridge 845, and a cap shoulder 844. The cap transition 840 can transition the electrode cap 835 from the cap top 841 to the dimensions of the outer cap edge 842. The cap transition can comprise a rounder portion, a sloped portion, a bevel, or other type of geometry that allows the cap top 841 to join with the outer cap edge 842. The cap shoulder 844 and the cap ridge 845 are configured to interact with an electrode wall of a flexible tip electrode as described throughout this application. The cap shoulder 844 and the cap ridge 845 can be coupled to the electrode wall. The electrode wall can be configured such that a distal end of the electrode wall surrounds the cap shoulder 844 to add support and stability after the electrode cap 835 has been secured to the electrode wall. The cap outer edge 842 can be sized to line up with the electrode wall when the electrode cap 835 has been coupled to electrode wall. The electrode cap 835 can further comprise a plurality of irrigation ports 836, a cap through-hole 848, and a plurality of halo irrigation openings, such as irrigation channels 837. The cap through hole can be used for placement of a sensor or other desired material within the electrode cap 835. In one embodiment a thermocouple or thermistor can be placed within the cap through-hole 848 and secured with a thermally conductive material. In other embodiments, the sensor can be coupled to the electrode cap 835 with a thermally conductive and electrically conductive material. In another embodiment the cap through-hole 848 can be fluidly coupled to the electrode cavity and fluid can flow therethrough.

The plurality of irrigation ports 836 can be equidistant from a longitudinal axis of the flexible tip electrode and evenly spaced from any surrounding irrigation ports. The plurality of irrigation channels 837 can be evenly spaced along the outer cap edge 842. As shown in FIG. 14, in some embodiments the each of the plurality of irrigation ports 836 can be next to and fluidly coupled to one of the irrigation channels 837. In the illustrated embodiment, every other irrigation channel 837 along the outer cap edge 842 can be coupled to one of the plurality of irrigation ports 836. Each of the plurality of irrigation channels 837 can further comprise a first channel side 851, a second channel side 852, and a channel wall 850. In the illustrated embodiment, a longitudinal axis of cap through-hole is perpendicular to a plane formed by the channel wall 850. In other embodiments, the channel wall 850 can be sloped such that a plane formed by the channel wall 850 can intersect with a longitudinal axis of the cap through-hole 848 at an angle. In one embodiment the plane formed by the channel wall 850 can intersect with the longitudinal axis of the cap through-hole 848 at an acute angle such that fluid flowing through the irrigation channel 837 flows in a more distal direction.

Although at least one embodiment of a tip electrode has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter tip electrode, comprising:
   a flexible electrode structure configured to flex upon application of an external force,
   wherein the flexible electrode structure comprises an electrode wall, an electrode cap, and a distal end portion defining a distal end, wherein the cap comprises a cap transition, wherein the electrode wall comprises a distal end, and wherein the distal end of the electrode wall can be coupled to the electrode cap; and
   a plurality of halo irrigation openings comprising a first channel side, a second channel side, an inner wall, and a channel wall, wherein the plurality of halo irrigation openings are configured to allow irrigant to pass therethrough in a circumferential pattern about the flexible electrode structure and proximate the distal end, wherein the channel wall comprises a slope in relation to a longitudinal axis of the catheter tip electrode configured to direct the irrigant in a more distal direction, wherein the inner wall extends along the longitudinal axis, wherein the channel wall intersects with the inner wall to form an angle, wherein at least one of the first channel side, the second channel side, and the channel wall form a plane, wherein the plurality of halo irrigation openings are disposed on the cap transition, and wherein the distal end of the electrode wall defines a proximal edge of at least one of the plurality of halo irrigation openings.

2. The catheter tip electrode according to claim 1 wherein the electrode cap comprises a plurality of irrigation ports and at least one irrigation slot, and wherein at least one of the plurality of halo irrigation openings comprises at least one irrigation slot.

3. The catheter tip electrode according to claim 2, wherein the at least one irrigation slot comprises eight irrigation slots.

4. The catheter tip electrode according to claim 3, wherein the eight irrigation slots are equally spaced around an outer cap edge of the electrode cap.

5. The catheter tip electrode according to claim 2, wherein the at least one irrigation slot is fluidly coupled to an inner cavity of the flexible electrode structure.

6. The catheter tip electrode according to claim 2, wherein the distal end portion further comprises a cap shoulder and a cap ridge.

7. The catheter tip electrode according to claim 6, wherein the cap shoulder and the cap ridge are configured to couple the electrode cap to the electrode wall.

8. The catheter tip electrode according to claim 2, wherein the electrode cap further comprises a cap through-hole.

9. The catheter tip electrode according to claim 8, wherein the cap through-hole extends from the cap bottom through the cap top.

10. A catheter tip assembly comprising:
    a flexible tip electrode comprising a proximal stem, an electrode wall, and an electrode cap, wherein the electrode cap comprises a cap transition, wherein the electrode wall comprises a distal end, and wherein the distal end of the electrode wall can be coupled to the electrode cap, wherein the electrode cap comprises a plurality of halo irrigation openings comprising a first channel side, a second channel side, an inner wall, and a channel wall, wherein the plurality of halo irrigation openings are configured to allow irrigant to pass therethrough in a circumferential pattern about the flexible electrode structure and proximate the distal end, wherein the channel wall comprises a slope in relation to a longitudinal axis of the catheter tip electrode configured to direct the irrigant in a more distal direction, wherein the inner wall extends along the longitudinal axis, wherein the channel wall intersects with the inner wall to form an angle, wherein at least one of the first channel side, the second channel side, and the channel wall form a plane, wherein the plurality of halo irrigation openings are positioned on the cap transition, and wherein the distal end of the electrode wall defines a proximal edge of at least one of the plurality of halo irrigation openings.

11. The catheter tip assembly according to claim 10, wherein the plurality of halo irrigation openings comprises four irrigation holes.

12. The catheter tip assembly according to claim 11, wherein the four irrigation holes are equally spaced along the cap transition.

13. The catheter tip assembly according to claim 10, wherein the electrode cap further comprises a cap through-hole.

14. A catheter assembly comprising:
a catheter body;
a flexible tip electrode comprising a proximal stem, an electrode wall, and an electrode cap, wherein the electrode cap comprises a cap transition and a distal end, wherein the distal end comprises a circumference, and wherein the cap transition is configured to transition the electrode cap from the circumference of the distal end to a dimension of the electrode wall, wherein the electrode wall comprises a distal end, and wherein the distal end of the electrode wall can be coupled to the electrode cap;

the electrode cap comprising a plurality of irrigation channels and a plurality of irrigation ports, wherein at least one of the plurality of irrigation ports comprises a first channel side, a second channel side, an inner wall, and a channel wall, wherein the channel wall comprises a slope in relation to a longitudinal axis of the flexible tip electrode configured to direct the irrigant in a more distal direction, wherein the inner wall extends along the longitudinal axis, wherein the channel wall intersects with the inner wall to form an angle, wherein at least one of the first channel side, the second channel side, and the channel wall form a plane, at least one of the plurality of irrigation ports is disposed on the cap transition, and wherein the distal end of the electrode wall defines a proximal edge of at least one of the plurality of irrigation ports, wherein the flexible tip electrode is coupled to a distal end of the catheter body.

15. The catheter assembly according to claim 14, wherein the electrode wall further comprises a linear gap that defines a plurality of interlocking blocks.

16. The catheter assembly according to claim 14, wherein a width of the plurality of irrigation channels is larger than a distally extending length of the plurality of irrigation channels.

17. The catheter assembly according to claim 14, wherein the electrode cap further comprises a cap through-hole.

18. The catheter assembly according to claim 14, wherein the electrode wall defines the proximal edge of the plurality of irrigation channels.

* * * * *